United States Patent [19]

Langhals

[11] Patent Number: 4,677,079

[45] Date of Patent: * Jun. 30, 1987

[54] PROCESS FOR DETERMINING THE COMPOSITION OF BINARY LIQUID MIXTURE

[76] Inventor: Heinz Langhals, Sundgauallee 55, D-7800 Freiburg, Fed. Rep. of Germany

[*] Notice: The portion of the term of this patent subsequent to Jun. 30, 2004 has been disclaimed.

[21] Appl. No.: 496,526

[22] Filed: May 24, 1983

Related U.S. Application Data

[63] Continuation of Ser. No. 322,636, Nov. 18, 1981, abandoned.

[30] Foreign Application Priority Data

Nov. 21, 1980 [DE] Fed. Rep. of Germany ....... 3043984

[51] Int. Cl.[4] ..................... G01N 33/00; G01N 33/18
[52] U.S. Cl. ...................................... 436/164; 436/40
[58] Field of Search ............... 250/373, 252; 356/409, 356/414; 436/39, 40, 164, 172

[56] References Cited

U.S. PATENT DOCUMENTS

3,742,429  7/1973  Kawai .................................. 356/409
3,874,794  4/1975  Schmitt et al.
4,267,572  5/1981  Witte ................................ 356/325 X

OTHER PUBLICATIONS

Hirt et al., Analytical Chemistry, vol. 26, No. 8, Aug. 1954, pp. 1270-1273.
ASTM, Manual on Recommended Practices in Spectrophotometry, 2nd Edition, 1966, General Techniques of Ultraviolet Quantitative Analysis, ASTM Designation: E 169-63, pp. 65-71.
K. Dimroth and C. Reinchardt, "Die colorimetrische Analyse binarer organischer Losungsmittelgemische mit Hilfe der Solvatochromie von Pyridinium-N-phenolbetainen", Z. Analyt, Chem., vol. 215, pp. 344-350, (1966).
C. Reichardt, "Empirische Parameter der Losungsmittelpolaritat als lineare 'Freie Enthalpie'—Beziehungen", Angewandte Chemie, vol. 91, pp. 119-131, (1979).
C. Reichardt and K. Dimroth, "Losungsmittel und empirische Parameter zur Charakterisierung ihrer Polaritat", Fortschritte der chemischen Forschung, vol. 11/1, pp. 1-73, (1968).
E. Kosower, "The Effect of Solvent on Spectra I. A New Empirical Measure of Solvent Polarity: Z-Values, II. Correlation of Spectral Absorption Data with Z-Values", Journal of American Chemical Society, vol. 80, pp. 3253-3270, (1958).
C. Reichardt, Solvent Effects in Organic Chemistry (Monographs in Modern Chemistry, vol. 3), pp. 189-195, (Weinham, New York: Verlag Chemie, 1979).
(List continued on next page.)

Primary Examiner—Arnold Turk
Attorney, Agent, or Firm—Robbins & Laramie

[57] ABSTRACT

The invention relates to a process for determining the composition of binary liquid mixtures. This process is characterized in that a solvatochromic compound is added to the sample to be analyzed, the solvatochromism band $\lambda_{max}$ is determined in the UV-spectrum, the $E_T$-value (molar stimulation energy) of the solvatochromic substance is calculated and the concentration of the more polar component is determined in accordance with the following equation $$c_P = c^* \exp(E_T/E_D - E_T°/E_D) - c^* \qquad (1)$$

in which $c_P$ represents the concentration of the more polar component, the component having the greater $E_T 30$-value being defined as the more polar component, $E_T$ represents the molar excitation energy of the solvatochromic compound, $E_T°$ represents the $E_T$-value of the pure, more apolar component, $E_T 30$ is the $E_T$-value using pyridinium phenol betaine and $c^*$ and $E_D$ are empirical parameters which may be taken from Tables or empirically determined.

10 Claims, 4 Drawing Figures

OTHER PUBLICATIONS

A. Vogel, *A Textbook of Quantitative Inorganic Analysis*, 4th Edition, pp. 687–690, (London: Longman, 1978).

M. Klessinger, "Konstitution und Lichtabsorption organischer Farbstoffe", *Chemie in unserer Zeit*, vol. 12, pp. 1–11, (1978).

Z. Maksimovic, C. Reichardt and A. Spiric, "Determination of Empirical Parameters of Solvent Polarity $E_T$ in Binary Mixtures by Solvatochromic Pyridinium-N-Phenol Betaine Dyes", *Z. Anal. Chem.*, vol. 270, pp. 100–104, (1974).

C. Reichardt and R. Muller, "Der Substituenteneinfluss auf das Elektronenanregungsspektrum der Pyridinium-N-phenolat-betaine", *Justus Liebigs Annalen Der Chemie*, No. 11, pp. 1937–1963, (1976).

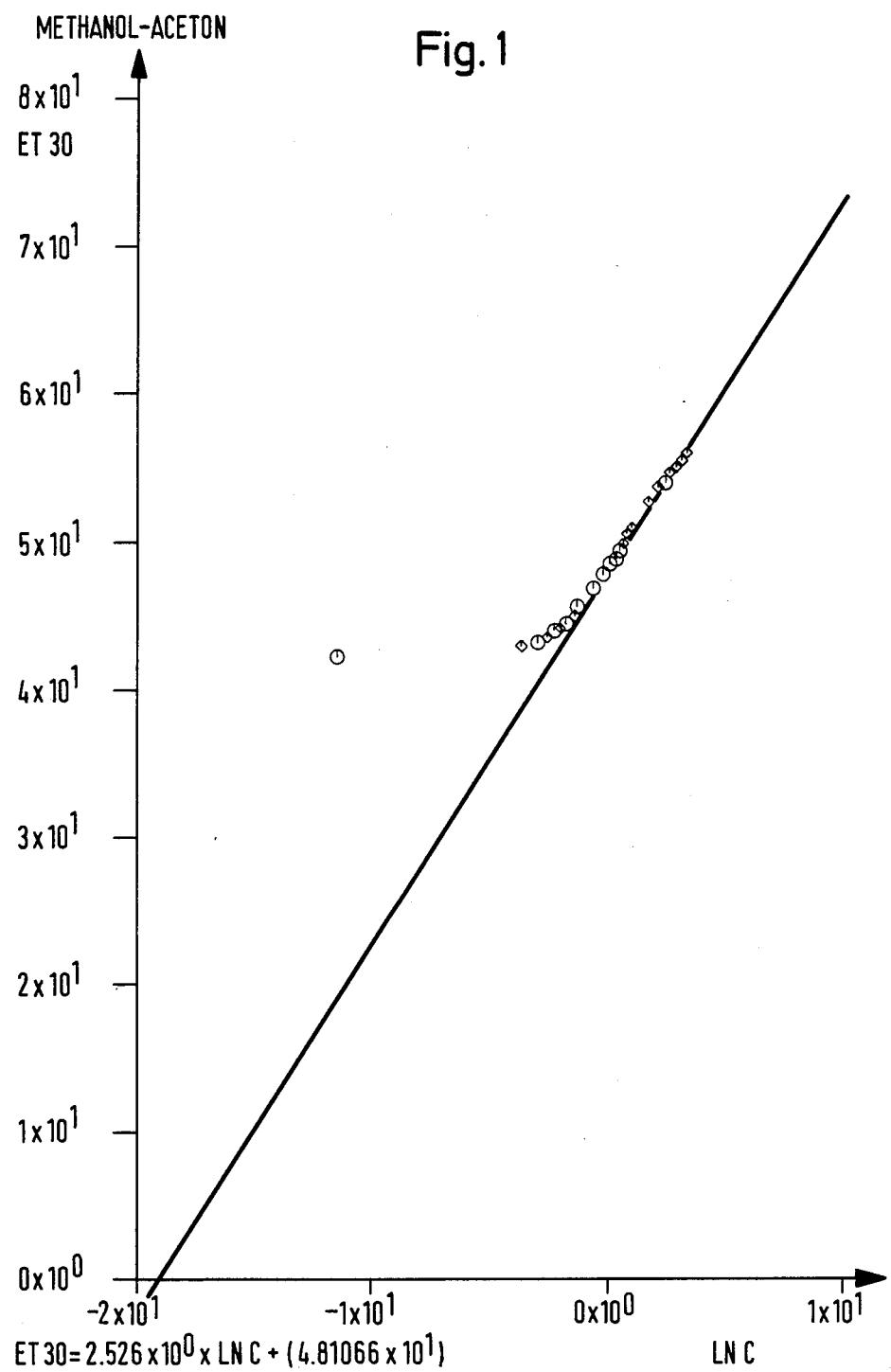

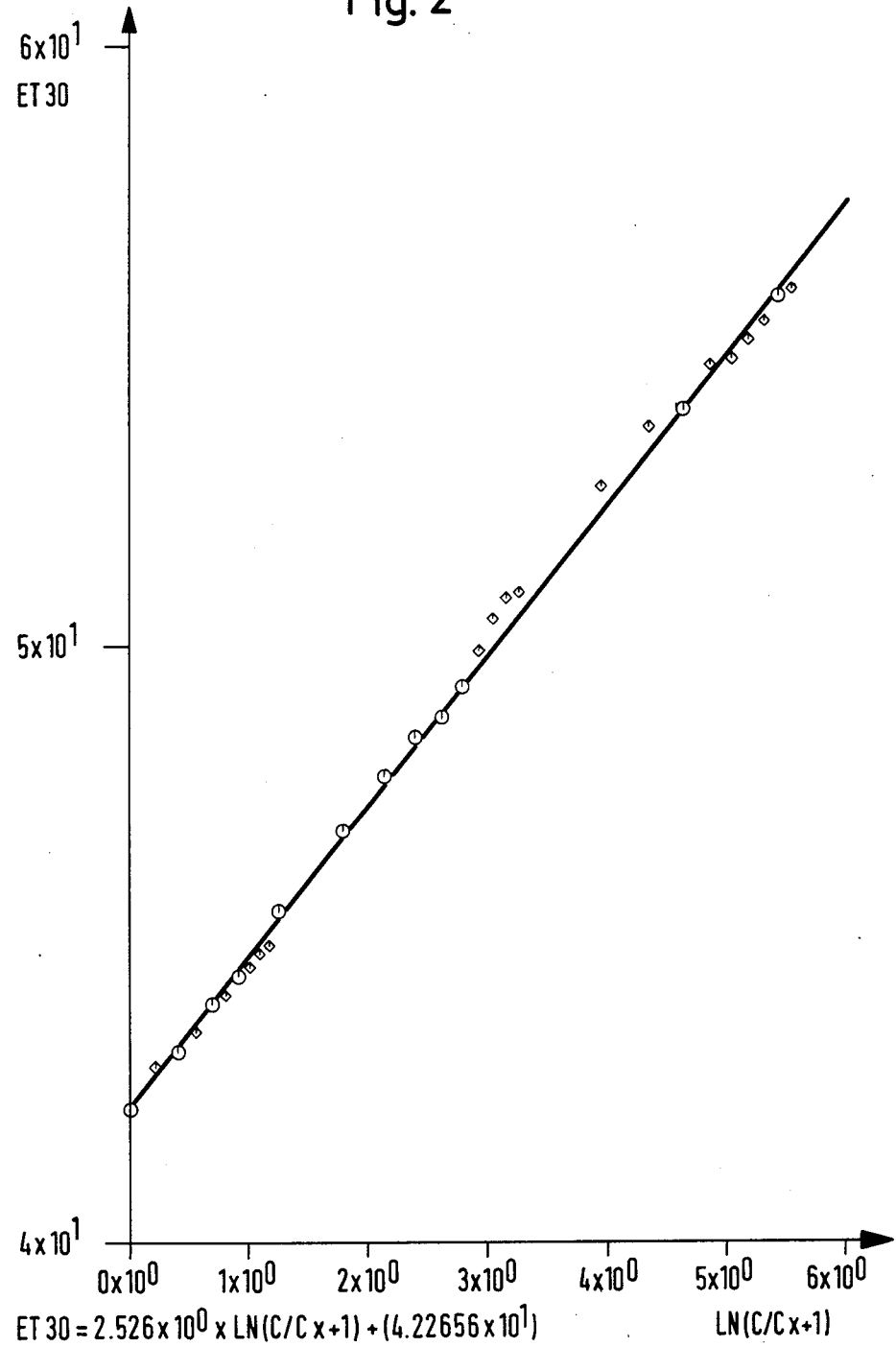

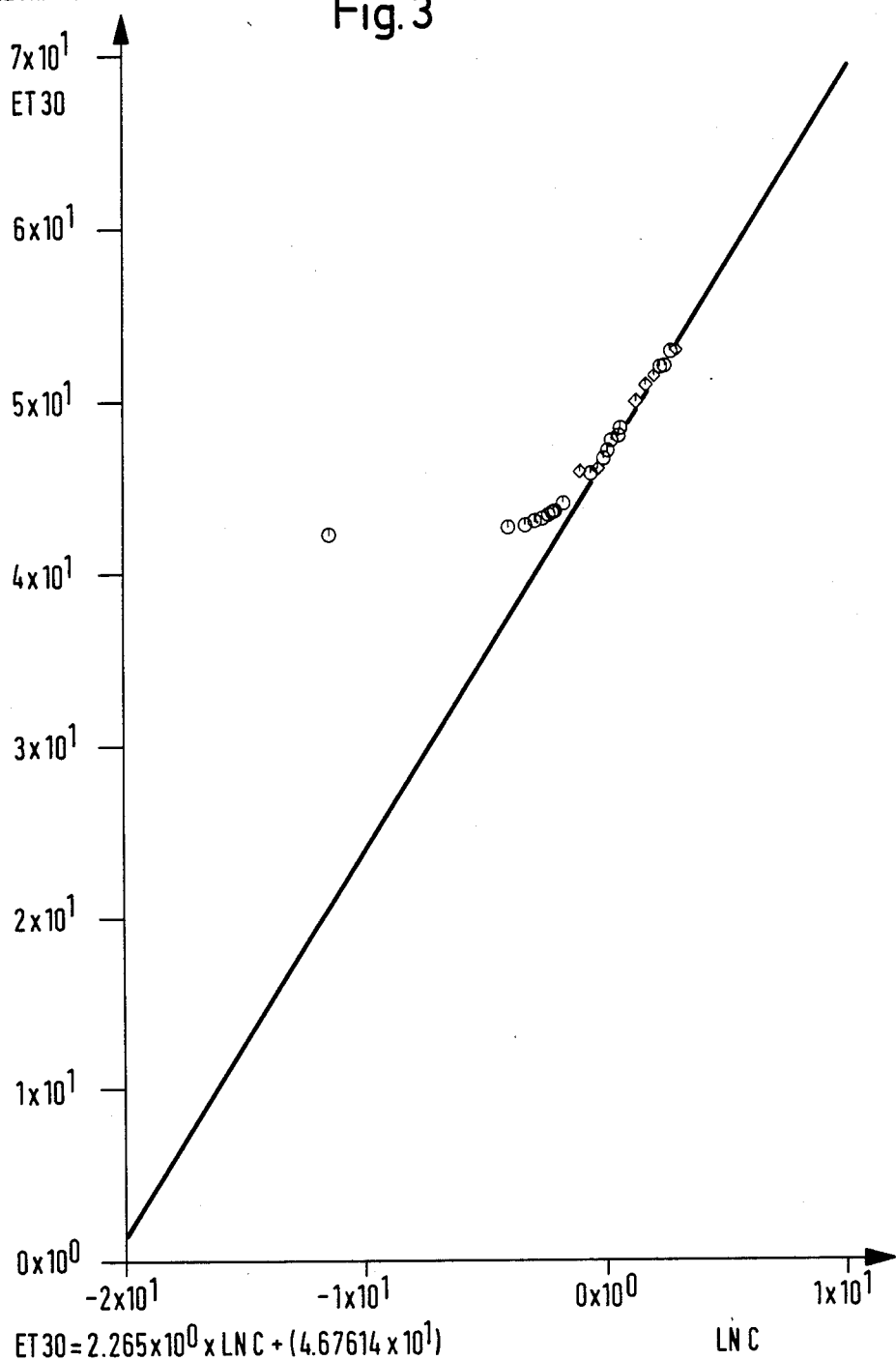

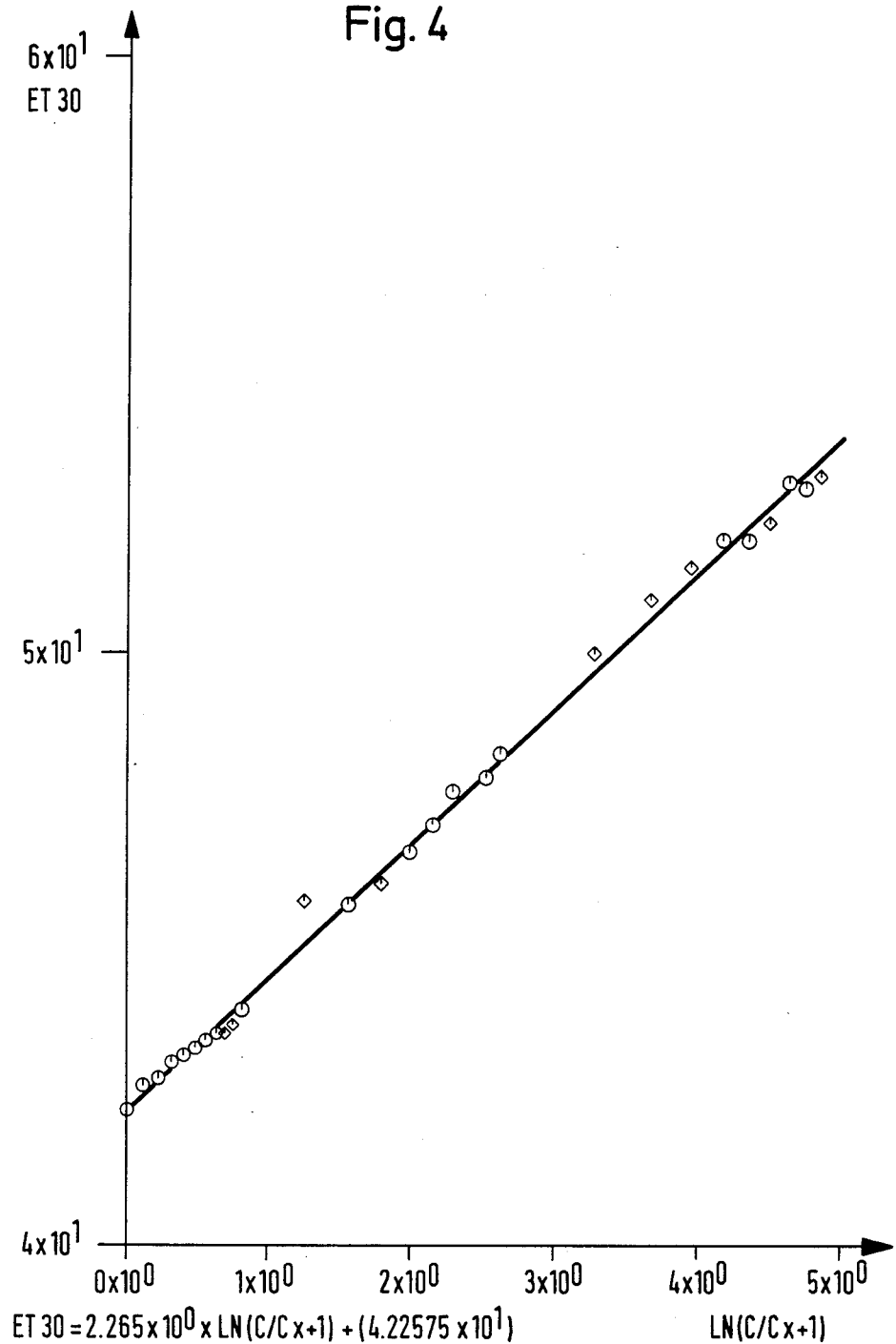

PROCESS FOR DETERMINING THE COMPOSITION OF BINARY LIQUID MIXTURE

This application is a continuation, of application Ser. No. 322,636, filed Nov. 18, 1981, now abandoned.

BACKGROUND OF THE INVENTION

This invention relates to a process for determining the composition of binary liquid mixtures by which the concentrations of the individual components may readily be determined.

PRIOR ART

K. Dimroth and C. Reichardt [Z. Analyt. Chem. 215, 344 (1966)] report on studies of binary solvent mixtures using solvatochromic dyes. These authors observed that the position of the longest-wave band in the UV-spectrum of solvatochromic substances is greatly influenced by the solvent used. This property has proved to be particularly useful for characterising the polarity of solvents. In apolar solvents, such as dioxane for example, pyridinium-N-phenol betaines for example absorb in the long-wave region, whilst in polar solvents, such as methanol for example, they absorb in the short-wave region. The maximum of this solvatochromic absorption is termed $\lambda_{max}$. The molar excitation energy $E_T$ may be calculated from the absorption wavelength $\lambda_{max}$ in accordance with the following equation:

$$E_T = 28{,}590 (\text{kcal} \cdot \text{nm} \cdot \text{mol}^{-1}) / \lambda_{max}.$$

The authors drew up calibration curves for nine mixtures of organic solvents with water. These calibration curves enable the water content of a mixture of unknown composition to be determined. However, this known process is attended by the disadvantage that calibration curves first have to be drawn up and that it is time-consuming and laborious.

The $E_T$-values used in the above process are generally suitable for characterising the polarity of organic solvents and the $E_T$-scale is now the most frequently used polarity scale [cf. K. Dimroth and C. Reichardt "Angewandte Chemie" 91, 119 (1979); K. Dimroth and C. Reichardt "Fortschritte der chemischen Forschung", Vol. 11/1, page 1 (1968)].

OBJECT OF THE INVENTION

The object of the present invention is to provide a simple and accurate rapid test for determining the composition of binary liquid mixtures.

SUMMARY OF THE INVENTION

The present invention relates to a process for determining the composition of binary liquid mixtures which is characterised in that a solvatochromic compound is added to the sample to be analysed, the solvatochromism band $\lambda_{max}$ in the UV-spectrum is determined, the $E_T$-value (molar excitation energy) of the solvatochromic substance is calculated and the concentration of the more polar component is determined in accordance with the following equation $$c_p = c^* \exp(E_T/E_D - E_T^\circ/E_D) - c^* \qquad (1)$$

in which
$c_p$ represents the concentration of the more polar component, the component having the greater $E_T 30$-value being defined as the more polar component, $E_T 30$ represents the molar excitation energy of pyridinium phenol betaine in the particular solvent, $E_T$ represents the molar excitation energy of the dye used and $E_T^\circ$ represents the $E_T$-value of the pure, more apolar component, $c^*$ and $E_D$ are empirical parameters which may be taken from Tables or empirically determined.

BRIEF DESCRIPTION OF THE FIGURES

FIG. 1 contains a plot of $E_T 30$ against in $c_p$ for a methanol-acetone mixture.

FIG. 2 contains a plot of $E_T 30$ against $\ln(c_p/c^* + 1)$ for a methanol-acetone mixture.

FIG. 3 contains a plot of $E_T 30$ against $\ln c_p$ for an ethanol-acetone mixture.

FIG. 4 contains a plot of $E_T 30$ against $\ln(c_p/c^* + 1)$ for an ethanol-acetone mixture.

DETAILED DESCRIPTION OF THE INVENTION

The Applicant has surprisingly found that, for all the binary systems studied, there is a connection between the $E_T$-values of solvatochromic substances and $c_p$ according to equation (1) above.

The $E_T$-values may be calculated from $\lambda_{max}$ of the solvatochromism band of the solvatochromic substances in accordance with the following equation $$E_T = 28{,}590 \; \text{kcal} \cdot \text{nm} \cdot \text{mol}^{-1} / \lambda_{max} \qquad (2)$$

To determine the $E_T$-values, the solvatochromic substance is dissolved in the sample to be analysed and $\lambda_{max}$ is measured in known manner. The concentrations are preferably selected in such a way that the extinctions at $\lambda_{max}$ lie in the extinction range from 0.4 to 1.2, preferably in the extinction range from 0.5 to 1.0 and, more preferably, in the extinction range from 0.7 to 1.0. Any suitable UV-spectrometer may be used for determining the $\lambda_{max}$-values.

Equation (1) is a two-parameter equation in which $c^*$ and $E_D$ may be determined for each binary solvent mixture by a simple procedure in which mixtures of the two samples to be analysed in known concentrations are prepared, a solvatochromic compound is added to the solutions and the $E_T$-values of these solutions are determined. The respective contents of the two components in the solutions are then converted into concentrations and, in a graph, the $E_T$-values obtained are plotted against ln $c_p$. The slope $E_D$ and the ordinate section b of the linear part are determined and $c^*$ is calculated in accordance with the following equation $$c^* = \exp[(E_T^\circ - b)/E_D] \qquad (3)$$

The concentrations may be converted into percent by weight in accordance with the following equation $$\% \text{ by weight} = c_p[\text{mol}/1] \cdot Mw_p / (\rho \text{solution}[\text{g/ml}] \cdot 10) \qquad (4)$$

in which
$Mw_p$ is the molecular weight of the more polar component and
$\rho$ is the density of the solution.

For frequently used solvents, the values $E_D$, c* are shown in Table I below. $E_T°$ is the value of the pure, more apolar component.

DETERMINATION OF THE VALUES OF TABLE I

The $E_T$-value is determined by a simple procedure. The pyridinium phenol betaine corresponding to the following formula

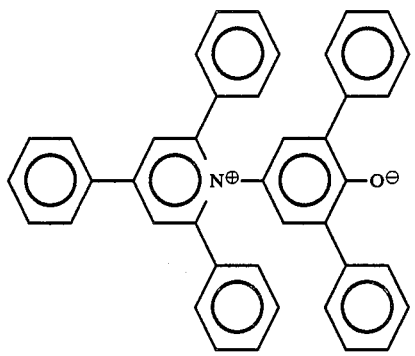

(I)

is dissolved in a small quantity (<5 mg) in the solvents to be studied. $\lambda_{max}$ of (I) in this solution is determined and the $E_T$-value is calculated with the aid of equation (2).

The solvatochromic substances used in accordance with the invention are the above-mentioned pyridinium phenol betaine corresponding to formula (I) or so-called Kosower's dye which corresponds to the following formula

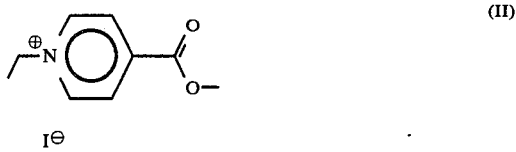

(II)

[E. M. Kosower, J. Am. Chem. Soc. 80, 3253 (1953)] or the solvatochromic substances which are described in C. Reichardt's book "Solvent Effects in Organic Chemistry", 1st Edition, Verlag Chemie Weinheim 1979, pages 193 and 194. It is particularly preferred to use the pyridinium phenol betained of formula (I).

Preferred components for binary mixtures are, in particular, the compounds described in Table (2) by C. Reichardt, "Angewandte Chemie" 91, pages 119 to 131 (1979), cf. in particular pages 124, 125.

The Applicant has studied numerous binary liquid mixtures and has found that, without exception, they may all be described by the equation observed.

The results obtained from 38 binary liquid mixtures are shown in Table I below. The $E_D$- and c*-values are quoted. Many different solvents were used in varying combinations.

TABLE I

Determination of $E_D$ and c* with the pyridinium phenol betaine of formula (I) in accordance with equation (1) for various solvent mixtures

| | Components[a] | $c_P^{(b,c)}$ | $E_T^{o(d,e)}$ | $c^{*(c,f)}$ | $E_D^{(d,f)}$ | $E_D^{(g)}$ | $r^{(h)}$ | $n^{(i)}$ |
|---|---|---|---|---|---|---|---|---|
| 1 | 1-butanol/acetone | 0.01–10.9 | 42.2 | 0.14 | 1.99 | 0.013 | 0.99952 | 31 |
| 2 | ethanol/acetone | 0.02–17.1 | 42.2 | 0.14 | 2.27 | 0.019 | 0.99939 | 28 |
| 3 | methanol/acetone | 0.03–24.7 | 42.2 | 0.10 | 2.53 | 0.019 | 0.99973 | 29 |
| 4 | water/acetone | 0.06–55.4 | 42.2 | 0.31 | 2.83 | 0.022 | 0.99963 | 29 |
| 5 | N—tert.-butyl formamide/acetone | 0.01–9.0 | 46.0 | 0.27 | 1.87 | 0.013 | 0.99948 | 31 |
| 6 | ethanol/acetonitrile | 0.01–17.1 | 46.0 | 0.10 | 1.83 | 0.012 | 0.99972 | 30 |
| 7 | 1-hexanol/acetonitrile | 0.01–8.0 | 46.0 | 0.08 | 1.08 | 0.019 | 0.99786 | 29 |
| 8 | methanol/acetonitrile | 0.03–24.7 | 46.0 | 0.06 | 1.83 | 0.033 | 0.99877 | 31 |
| 9 | water/acetonitrile | 0.06–49.8 | 46.0 | 0.15 | 2.07 | 0.024 | 0.99877 | 27 |
| 10 | N—tert.-butylformamide/benzene | 0.01–9.0 | 34.5 | 0.01 | 2.27 | 0.031 | 0.99851 | 31 |
| 11 | water/tert.-butyl alcohol | 0.06–33.2 | 43.9 | 1.01 | 2.82 | 0.050 | 0.99666 | 26 |
| 12 | water/tert.-butyl hydroperoxide | 0.4–7.4 | 49.7 | 0.312 | 1.40 | 0.021 | 0.99922 | 12 |
| 13 | water/dimethyl formamide | 0.06–38.8 | 43.8 | 11.43 | 9.24 | 0.18 | 0.99527 | 27 |
| 14 | acetonitrile/1,4-dioxane | 0.02–19.1 | 36.0 | 0.77 | 3.23 | 0.031 | 0.99909 | 29 |
| 15 | 1-butanol/1,4-dioxane | 0.01–10.1 | 36.0 | 0.90 | 5.39 | 0.026 | 0.99973 | 30 |
| 16 | ethanol/1,4-dioxane | 0.02–17.1 | 36.0 | 0.72 | 4.99 | 0.030 | 0.99975 | 30 |
| 17 | methanol/1,4-dioxane | 0.03–24.7 | 36.0 | 0.35 | 4.55 | 0.037 | 0.99922 | 30 |
| 18 | nitromethane/1,4-dioxane | 0.02–18.6 | 36.0 | 1.01 | 3.49 | 0.026 | 0.99929 | 31 |
| 19 | pinacolone/1,4-dioxane | 0.2–8.0 | 36.0 | 3.43 | 3.33 | 0.16 | 0.98025 | 19 |
| 20 | propionitrile/1,4-dioxane | 0.01–14.1 | 36.0 | 1.41 | 3.33 | 0.038 | 0.99834 | 30 |
| 21 | water/1,4-dioxane | 0.6–55.4 | 36.0 | 0.58 | 4.34 | 0.054 | 0.99922 | 22 |
| 22 | 1-butanol/nitromethane | 0.01–10.9 | 46.3 | 0.06 | 1.43 | 0.015 | 0.99914 | 31 |
| 23 | ethanol/nitromethane | 0.02–17.1 | 46.3 | 0.03 | 1.41 | 0.030 | 0.99704 | 30 |
| 24 | methanol/nitromethane | 0.03–22.2 | 46.3 | 0.01 | 1.66 | 0.018 | 0.99947 | 29 |
| 25 | acetone/pyridine | 0.03–12.2 | 40.2 | 32.06 | 4.01 | 0.13 | 0.98710 | 28 |
| 26 | 1-dodecanol/pyridine | 0.004–4.5 | 40.2 | 0.89 | 2.90 | 0.03 | 0.99901 | 30 |
| 27 | ethanol/pyridine | 0.02–17.1 | 40.2 | 12.75 | 9.64 | 0.17 | 0.99554 | 31 |
| 28 | 1-hexanol/pyridine | 0.01–8.0 | 40.2 | 1.11 | 2.90 | 0.047 | 0.99763 | 30 |
| 29 | methanol/pyridine | 0.03–24.7 | 40.2 | 5.84 | 6.92 | 0.081 | 0.99802 | 31 |
| 30 | nitromethane/pyridine | 0.02–18.6 | 40.2 | 13.62 | 6.46 | 0.14 | 0.99384 | 30 |
| 31 | tert.-pentyl alcohol/pyridine | 0.005–8.3 | 40.2 | 0.95 | 1.02 | 0.025 | 0.99341 | 29 |
| 32 | water/pyridine | 0.06–49.8 | 40.2 | 5.48 | 7.09 | 0.12 | 0.99599 | 29 |
| 33 | 1-butanol/$CS_2$ | 0.01–10.9 | 32.6 | 0.03 | 2.42 | 0.028 | 0.99906 | 36 |
| 34 | 1,4-dioxane/$CS_2$ | 0.01–11.7 | 32.6 | 1.96 | 1.21 | 0.049 | 0.98083 | 31 |

TABLE I-continued

Determination of $E_D$ and $c^*$ with the pyridinium phenol betaine of formula (I) in accordance with equation (1) for various solvent mixtures

| Components[a] | $c_p$[b,c] | $E_T^o$[d,e] | $c^*$[c,f] | $E_D$[d,f] | $E_D$[g] | $r$[h] | $n$[i] |
|---|---|---|---|---|---|---|---|
| 35 1-octanol/CS$_2$ | 0.01–6.4 | 32.6 | 0.06 | 2.83 | 0.055 | 0.99676 | 30 |
| 36 pinacolone/CS$_2$ | 0.3–8.0 | 32.6 | 7.89 | 9.30 | 0.26 | 0.99459 | 16 |
| 37 methanol/acetone[m] | 0.03–24.7 | 66.3[m] | 0.65 | 4.66 | 0.014 | 0.99993 | 11 |
| 38 methanol/1,4-dioxane[m] | 0.03–24.7 | 63.0[m] | 2.66 | 8.52 | 0.18 | 0.99384 | 31 |

[a]The more polar solvent is named first.
[b]Concentration range studied.
[c]In mol · l$^{-1}$
[d]In kcal · mol$^{-1}$
[e]$E_T$30-value of the more apolar solvent (cf. also lit.)
[f]See text.
[g]Variance of $E_D$
[h]Correlation coefficient where equation (3) is applied.
[i]Number of measuring points.
[m]Using Kosower's dye.

The new analysis process may be carried out with all kinds of binary systems. The samples to be analysed may be mixtures of aliphatic, cycloaliphatic and aromatic hydrocarbons, alcohols, ketones, nitriles, aldehydes, sulfur compounds such as, for example, sulfoxides, sulfones and mercaptans, of esters such as, for example, carboxylic acid esters, lactones and sulfonic acid esters, ethers, acetals and ketals, oximes, heterocyclic compounds, nitrogen compounds such as, for example, amines, amides, hydrazines and lactams, phosphorus compounds such as, for example, phosphines, phosphine oxides, phosphorous acids esters and phosphoric acid esters and substituted derivatives thereof. There are virtually no limitations in regard to the nature of the binary mixtures to be analysed. It is also possible to analyse mixtures of water and the above-mentioned solvents, as described in the applicant's copending application Ser. No. 322,571, filed simultaneously with the present application on Nov. 18, 1981 now abandoned and titled "A Process for Determining Water in Samples Containing Water.

The new analysis process may be used for example in studies of the composition of monomer mixtures in copolymerisation reactions, in studies of the composition of solvent mixtures in the manufacture of dyes, lacquers and pharmaceutical products and—generally—in the analysis of mixtures of the type used in chemical syntheses and in the working up of extractants and flotation agents. Because it is highly specific, it may be used as a process for testing purity.

The sole limitation exists in cases where binary mixtures containing components of very similar polarity are used. In that case, the change in the measured value ($\lambda_{max}$ or $E_T$) accompanying any change in the composition of the solvent is so small that exact content determination is no longer possible.

Another remarkable feature is that the two components of the binary mixture do not have to be liquid. The equation that has been found even applies to the liquid component of a mixture of a solid with a liquid or of two solids.

Accordingly, the composition of numerous samples to be analysed may be determined by the process according to the invention. For example, the solvent content of liquid, gaseous and solid samples may be determined by the process according to the invention. In the case of liquid samples, the solvent content is directly determined in accordance with equation (1) using a solvatochromic dye.

Gaseous samples may also be analysed. In order for example to determine the solvent content (LM1) of a gas, a specific volume of the gas is passed through a second high-boiling solvent (LM2) which washes out the first solvent. The solvent content of the gas may be determined by calculating the content of LM1 in LM2 in accordance with (1).

It is also possible to analyse solid samples. For example, the water content or the content of a certain solvent in polymeric naturally occurring materials, such as for example starch, cellulose, in synthetic polymers, in pharmaceutical preparations and solvent-binding substances, such as for example salts, etc., may be determined in accordance with the invention.

If dispersions or suspensions are analysed by the process according to the invention, it is important to ensure that some of the light transmitted through is scattered. Although this phenomenon does not in any way change the position of $\lambda_{max}$, it can complicate the measurement. In a case such as this, it may be necessary to use a sensitive spectrometer for determining $\lambda_{max}$.

The process according to the invention may be carried out at room temperature. For determining the Table values and in cases where highly accurate analytical results are required, it is preferred to carry out the process according to the invention at a constant temperature. However, this is not absolutely necessary because the effect of temperature on the process according to the invention remains within very narrow limits.

The process according to the invention may be carried out at any temperatures at which the dye used is heat-stable. At very high temperatures above the boiling point of the mixture, the process becomes complicated.

In one particularly preferred simplified embodiment of the invention, analysis in accordance with equation (1) is carried out by visual colour comparison with a colour scale. To this end, the absorption colour of the solution or dispersion is visually compared with a colour scale (absorption colour as a function of $\lambda_{max}$ of the absorption) and $\lambda_{max}$ absorption is determined on the basis of this comparison.

The process according to the invention may also be carried out by absorbing the solvatochromic dyes onto solids, for example paper, so that test strips are obtained. These test strips are dipped into the solution to be analysed. The test strips change colour according to the content of the individual components. $\lambda_{max}$ is determined by a colour comparison with a colour scale ($\lambda$ as a function of the absorption colour) and $c_p$ is calculated in accordance with equation (1).

It is of particular importance to the result that there is a logarithmic relationship between the $E_T$-values and $c_p$ according to equation (1). Accordingly, the relative accuracy of the determination of $c_p$ is constant over a wide concentration range. $c_p$ may even be determined with great accuracy where the more polar component is present in low concentrations The invention is illustrated by the following Examples.

In the Examples, the UV-spectra are recorded by means of a Zeiss DMR21 UV-spectrophotometer. Visual comparison of the solution with a colour scale is sufficient for an approximate determination of concentration.

EXAMPLE 1

General procedure for determining the composition of binary liquid mixtures

Quantities of 0.1, 1, 2 ... ml of the more polar component of the binary mixture are introduced into a 10 ml measuring flask. The measuring flask is made up to 10 ml with the other component. A small quantity (<5 mg) of the phenol betaine of formula (I) is added to the solvent mixture and the position of the solvatochromism band $\lambda_{max}$ is determined in the UV-spectrum at 25° C. The concentrations are intended to be selected in such a way that $\lambda_{max}$ lies in the extinction range of 0.7 ... 1.0. For accurately locating $\lambda_{max}$, the point at which the line connecting the radii intersects the absorption curve may be determined in accordance with the Mathias rule.

$\lambda_{max}$ is converted in accordance with equation (2) into the $E_T$-value which is subsequently introduced into equation (1) with the values $E_T°$, $c^*$ and $E_D$ of Table I and $c_p$ calculated.

In a graph, $E_T$ is plotted against $\ln c_p$ and the slope $E_D$ and the ordinate section b of the linear part are determined. $c^*$ is calculated in accordance with equation (3), as indicated in the specification.

The POLAR computer program is available for this procedure; this program also takes into account measured values in the non-linear part of the graph.

EXAMPLE 2

Special procedure for determining the parameters $E_D$ and $c^*$ of the "methanol-acetone" system Following the procedure described in Example 1, the milliliters of methanol indicated in Table 2 below are pipetted into a 10 ml measuring flask. The flask is then made up to 10 ml with acetone. The phenol betaine of formula (I) is dissolved in a small quantity (<5 mg) in the solutions obtained, after which $\lambda_{max}$ is measured. The milliliters introduced are converted into the concentration in mol·l$^{-1}$ $c_p$ of methanol and the $\lambda_{max}$-values are converted into $E_T30$. $\ln c_p$ is then calculated. The results obtained are shown in Table 2.

TABLE II

| ml methanol | $\lambda_{max}$ | $c_p$ (mol/l) | $E_T30$ | $\ln c_p$ |
| --- | --- | --- | --- | --- |
| 0.00 | 677.0 | 0.000 | 42.2 | −11.51 |
| 0.01 | 666.0 | 0.025 | 42.9 | −3.70 |
| 0.02 | 662.0 | 0.049 | 43.2 | −3.01 |
| 0.03 | 657.0 | 0.074 | 43.5 | −2.60 |
| 0.04 | 650.0 | 0.099 | 44.0 | −2.31 |
| 0.05 | 648.0 | 0.123 | 44.1 | −2.09 |
| 0.06 | 643.0 | 0.148 | 44.5 | −1.91 |
| 0.07 | 641.0 | 0.173 | 44.6 | −1.76 |
| 0.08 | 638.0 | 0.198 | 44.8 | −1.62 |
| 0.09 | 636.0 | 0.222 | 45.0 | −1.50 |
| 0.10 | 628.0 | 0.247 | 45.5 | −1.40 |
| 0.20 | 610.0 | 0.494 | 46.9 | −0.71 |
| 0.30 | 598.0 | 0.741 | 47.8 | −0.30 |

TABLE II-continued

| ml methanol | $\lambda_{max}$ | $c_p$ (mol/l) | $E_T30$ | $\ln c_p$ |
| --- | --- | --- | --- | --- |
| 0.40 | 590.0 | 0.988 | 48.5 | −0.01 |
| 0.51 | 586.0 | 1.260 | 48.8 | 0.23 |
| 0.61 | 580.0 | 1.507 | 49.3 | 0.41 |
| 0.71 | 573.0 | 1.754 | 49.9 | 0.56 |
| 0.80 | 567.0 | 1.976 | 50.4 | 0.68 |
| 0.90 | 563.0 | 2.223 | 50.8 | 0.80 |
| 1.00 | 562.0 | 2.470 | 50.9 | 0.90 |
| 2.00 | 543.0 | 4.940 | 52.7 | 1.60 |
| 3.00 | 533.0 | 7.410 | 53.6 | 2.00 |
| 4.00 | 530.0 | 9.880 | 53.9 | 2.29 |
| 5.00 | 523.0 | 12.350 | 54.7 | 2.51 |
| 6.00 | 522.0 | 14.820 | 54.8 | 2.70 |
| 7.00 | 519.0 | 17.290 | 55.1 | 2.85 |
| 8.00 | 516.0 | 19.760 | 55.4 | 2.98 |
| 9.00 | 512.0 | 22.230 | 55.8 | 3.10 |
| 10.00 | 511.0 | 24.700 | 55.9 | 3.21 |

The measurements were carried out at a temperature of 298.00° K. and the starting conditions were as follows:
* Concentration factor: 2.470
Energy factor: 28590
$c^*$: 0.1
Number of measured values: 29

In FIG. 1, $E_T30$ is plotted against $\ln c_p$ and a straight line drawn through the linear part of the curve. The slope $E_D$ of the straight line amounts to 2.53.

The ordinate section b has a value of 48.1, as reported in FIG. 1.

According to C. Reichardt "Angewandte Chemie" 91, 119 (1979), 42.2 kcal·mol$^{-1}$ is the $E_T°$-value.

$c^*$ is calculated in accordance with formula (3):

$$c^* = \exp[(E_T° - b)/E_D] \rightarrow c^* = 0.097 \text{ mol·l}^{-1}$$

The more exact value for $c^*$ is calculated using the POLAR computer program:

$$c^* = 0.099 \text{ mol·l}^{-1}$$

It is now possible to analyse any mixtures with the aid of the calculated values $c^*$ and $E_D$ for the methanol-acetone mixture.

The results obtained are shown in Table III.

The results of the machine evaluation of the methanol-acetone system are shown in FIG. 2.

TABLE III

| c(Mol/l) | $E_T30$ | $\ln(c + c^*)$ | $\ln(c/c^* + 1)$ |
| --- | --- | --- | --- |
| 0.000 | 42.2 | −2.31 | 0.00 |
| 0.025 | 42.9 | −2.09 | 0.22 |
| 0.049 | 43.2 | −1.91 | 0.40 |
| 0.074 | 43.5 | −1.75 | 0.56 |
| 0.099 | 44.0 | −1.62 | 0.69 |
| 0.123 | 44.1 | −1.50 | 0.81 |
| 0.148 | 44.5 | −1.40 | 0.92 |
| 0.173 | 44.6 | −1.30 | 1.01 |
| 0.198 | 44.8 | −1.22 | 1.10 |
| 0.222 | 45.0 | −1.14 | 1.18 |
| 0.247 | 45.5 | −1.06 | 1.25 |
| 0.494 | 46.9 | −0.52 | 1.79 |
| 0.741 | 47.8 | −0.17 | 2.14 |
| 0.988 | 48.5 | 0.08 | 2.40 |
| 1.260 | 48.8 | 0.31 | 2.62 |
| 1.507 | 49.3 | 0.47 | 2.79 |
| 1.754 | 49.9 | 0.62 | 2.93 |
| 1.976 | 50.4 | 0.73 | 3.04 |
| 2.223 | 50.8 | 0.84 | 3.16 |
| 2.470 | 50.9 | 0.94 | 3.26 |
| 4.940 | 52.7 | 1.62 | 3.93 |
| 7.410 | 53.6 | 2.02 | 4.33 |
| 9.880 | 53.9 | 2.30 | 4.61 |
| 12.350 | 54.7 | 2.52 | 4.83 |
| 14.820 | 54.8 | 2.70 | 5.02 |
| 17.290 | 55.1 | 2.86 | 5.17 |
| 19.760 | 55.4 | 2.99 | 5.30 |
| 22.230 | 55.8 | 3.11 | 5.42 |

TABLE III-continued

| c(Mol/l) | $E_T30$ | ln (c+ c*) | ln (c/c* + 1) |
|---|---|---|---|
| 24.700 | 55.9 | 3.21 | 5.52 |

Correlation coefficient: 0.99973
Sigma $E_D$: 0.018693

EXAMPLE 3

Procedure for determining the content of methanol in a mixture of methanol and acetone of unknown concentration The phenol betaine of formula (I) is dissolved in a mixture of methanol and acetone and $\lambda_{max}$ is determined.

$\lambda_{max}$ amounts to 610 nm.

$$\rightarrow E_T30 = 46.9 \text{ kcal·mol}^{-1}$$

The following values are calculated in accordance with equation (1):

$$c_p = c^* \exp(E_T/E_D - E_T°/E_D) - c^*$$

$$c_p = 0.535 \text{ mol·l}$$

$$E_D = 2.53 \text{ kcal·mol}^{-1}$$

$$c^* = 0.099 \text{ mol·l}^{-1}$$

$$E_T° = 42.2 \text{ kcal·mol}^{-1}$$

Accordingly, the mixture to be studied contained 0.54 mol·l$^{-1}$ of methanol; the set value of $c_p$ was 0.494. The rest was acetone. The accuracy with which $c_p$ is determined may be further increased by using a better spectrometer.

EXAMPLE 4

A mixture of ethanol and acetone is studied by the process described in Example 2.

$E_D$, b and c* are determined in the same way as described above.

Ethanol is the more polar component.

$$E_D = 2.27 \text{ kcal·mol}^{-1}$$

$$C^* = 0.137 \text{ mol·l}^{-1}$$

$$b = 46.8 \text{ kcal·mol}^{-1}$$

$$E_T° = 42.2 \text{ kcal·mol}^{-1}$$

($E_T30$-value of acetone according to C. Reichardt "Angewandte Chemie" 91, 119, (1979)).

The results obtained are shown in Tables IV and V and in FIG. 3 (manual evaluation) and in FIG. 4 (machine evaluation).

TABLE IV

| ml ethanol | $\lambda_{max}$ (nm) | $c_p$ (Mol/l) | $E_T30$ | ln $c_p$ |
|---|---|---|---|---|
| 0.00 | 677.5 | 0.000 | 42.2 | $-\infty$ |
| 0.01 | 670.0 | 0.017 | 42.7 | −4.07 |
| 0.02 | 668.0 | 0.034 | 42.8 | −3.37 |
| 0.03 | 664.0 | 0.051 | 43.1 | −2.97 |
| 0.04 | 662.0 | 0.069 | 43.2 | −2.68 |
| 0.05 | 660.0 | 0.086 | 43.3 | −2.46 |
| 0.06 | 658.0 | 0.103 | 43.4 | −2.27 |
| 0.07 | 656.0 | 0.120 | 43.6 | −2.12 |
| 0.08 | 656.0 | 0.137 | 43.6 | −1.99 |
| 0.09 | 654.0 | 0.154 | 43.7 | −1.87 |
| 0.10 | 650.0 | 0.171 | 44.0 | −1.76 |
| 0.20 | 624.0 | 0.343 | 45.8 | −1.07 |
| 0.30 | 625.0 | 0.514 | 45.7 | −0.67 |
| 0.40 | 620.0 | 0.685 | 46.1 | −0.38 |
| 0.50 | 613.0 | 0.857 | 46.6 | −0.15 |
| 0.60 | 607.0 | 1.028 | 47.1 | 0.03 |
| 0.70 | 600.0 | 1.199 | 47.6 | 0.18 |
| 0.90 | 597.0 | 1.542 | 47.9 | 0.43 |
| 1.00 | 592.0 | 1.713 | 48.3 | 0.54 |
| 2.00 | 572.0 | 3.427 | 50.0 | 1.23 |
| 3.00 | 562.0 | 5.140 | 50.9 | 1.64 |
| 4.00 | 556.0 | 6.853 | 51.4 | 1.92 |
| 5.00 | 551.0 | 8.566 | 51.9 | 2.15 |
| 6.00 | 551.0 | 10.280 | 51.9 | 2.33 |
| 7.00 | 548.0 | 11.993 | 52.2 | 2.48 |
| 8.00 | 541.0 | 13.706 | 52.8 | 2.62 |
| 9.00 | 542.0 | 15.420 | 52.7 | 2.74 |
| 10.00 | 540.0 | 17.133 | 52.9 | 2.84 |

Starting conditions:
Concentration factor: 1.713
Energy factor: 28590
c*: 0.1
Number of measured values: 28

TABLE V

| $c_p$ (Mol/l) | $E_T30$ | ln (c+ c*) | ln (c/c* + 1) |
|---|---|---|---|
| 0.000 | 42.2 | −1.99 | 0.00 |
| 0.017 | 42.7 | −1.87 | 0.12 |
| 0.034 | 42.8 | −1.77 | 0.22 |
| 0.051 | 43.1 | −1.67 | 0.32 |
| 0.069 | 43.2 | −1.58 | 0.41 |
| 0.086 | 43.3 | −1.50 | 0.49 |
| 0.103 | 43.4 | −1.43 | 0.56 |
| 0.120 | 43.6 | −1.36 | 0.63 |
| 0.137 | 43.6 | −1.29 | 0.69 |
| 0.154 | 43.7 | −1.23 | 0.75 |
| 0.171 | 44.0 | −1.18 | 0.81 |
| 0.343 | 45.8 | −0.73 | 1.25 |
| 0.514 | 45.7 | −0.43 | 1.56 |
| 0.685 | 46.1 | −0.20 | 1.79 |
| 0.857 | 46.6 | −0.01 | 1.98 |
| 1.028 | 47.1 | 0.15 | 2.14 |
| 1.199 | 47.6 | 0.29 | 2.28 |
| 1.542 | 47.9 | 0.52 | 2.51 |
| 1.713 | 48.3 | 0.62 | 2.60 |
| 3.427 | 50.0 | 1.27 | 3.26 |
| 5.140 | 50.9 | 1.66 | 3.65 |
| 6.853 | 51.4 | 1.94 | 3.93 |
| 8.566 | 51.9 | 2.16 | 4.15 |
| 10.280 | 51.9 | 2.34 | 4.33 |
| 11.993 | 52.2 | 2.50 | 4.48 |
| 13.706 | 52.8 | 2.63 | 4.62 |
| 15.420 | 52.7 | 2.74 | 4.73 |
| 17.133 | 52.9 | 2.85 | 4.84 |

Correlation coefficient: 0.99939
Sigma $E_D$: 0.019

EXAMPLE 5

Analysis of a mixture of ethanol and acetone of unknown concentration

A mixture of ethanol and acetone of unknown concentration is studied by the process described in Example 3.

$$\lambda_{max} = 650 \text{ nm} \rightarrow E_{T^+} = 44.0 \rightarrow c_p = 0.166 \text{ mol·l}^{-1};$$

the set value was 0.171 mol·l$^{-1}$

The mixture to be studied contains 0.166 mol·l$^{-1}$ of ethanol. The rest is acetone.

What is claimed is:

1. In a process for determining the composition of an anhydrous mixture of two materials of different polarities, at least one of which is a liquid organic solvent, wherein a solvatochromic compound is added to the mixture and the $\lambda_{max}$ values are determined in the UV spectrum, and wherein the $E_T$ values are calculated from the $\lambda_{max}$ values, and wherein the $E_T^\circ$ value of the less polar of said materials is known or determined, the improved process comprising determining standard reference values by preparing several anhydrous mixtures of said two materials, said mixtures having different respective contents of said two materials, adding the same amount of a solvatochromic compound to each said mixture, then obtaining the $\lambda_{max}$ value for each in the extinction range from 0.4 to 1.2, calculating the $E_T$ value for each said prepared mixture from its $\lambda_{max}$ value, calculating the molar concentration of the more polar of said materials in each said prepared mixture, plotting the $E_T$ values against the values of the logarithms of the concentrations by weight of said mixtures, $c_p$, of the more polar of said two materials along the oridinate and along the abcissa, respectively, and drawing a straight line through the linear part of said plotted values, determining the slope $E_D$ of said straight line, determining the value "b" of the oridinate section measured on the ordinate, at the point on said straight line at the zero value of the logarithm of the concentration $c_p$ of the more polar of said materials, then:

adding said amount of said solvatochromic compound to, and obtaining the $\lambda_{max}$ for, said unknown mixture, calculating the $E_T$ value for said unknown mixture using its observed $\lambda_{max}$, calculating the value of a constant, $c^*$, according to the equation:

$$c^* = e(E_T^\circ - b)/E_D]$$

and then calculating the molar concentration of said more polar material based on the unknown mixture according to the equation $$c_p = c^*(E_T/E_D - E_T^\circ/E_D) - c^*$$

where $E_T$ in the equation is the $E_T$ calculated for said unknown mixture from its said observed $\lambda_{max}$.

2. The process of claim 1 wherein the $E_T$ value of said unknown mixture is calculated according to the equation $$E_T = 28{,}590\ Kcal \cdot nm \cdot mol^{-1}/\lambda_{max}.$$

3. The process of claim 2 wherein the $\lambda_{max}$ lies in the extinction range of from 0.6 to 1.0.

4. The process of claim 2 wherein the solvatochromic compound is a pyridinium phenol betaine of the formula

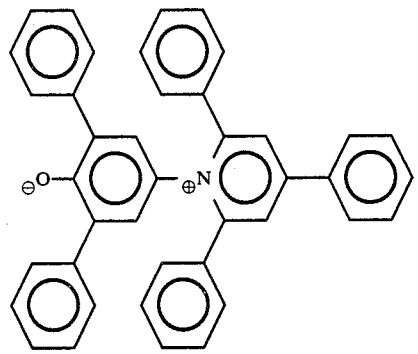

or a Kosower's dye of the formula

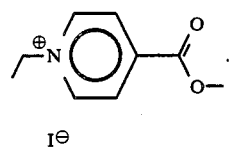

5. The process of claim 1 wherein both of said materials are liquid organic solvents.

6. The process of claim 5 wherein the $\lambda_{max}$ lies in the extinction range of from 0.6 to 1.0.

7. The process of claim 5 wherein the concentration of the more polar component determination is carried out by a visual color comparison with a color scale.

8. The process of claim 5 wherein the solvatochromic compound is absorbed to a solid material and the concentration of the more polar component determination is carried out with this material.

9. The process of claim 5 wherein the solvatochromic compound is a pyridinium phenol betaine of the formula

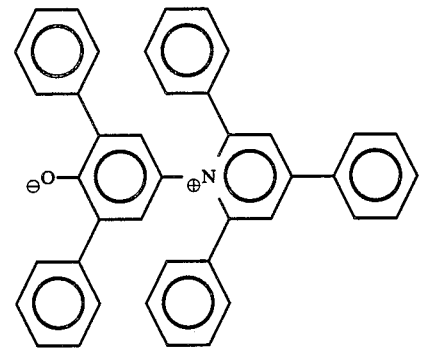

or a Kosower's dye of the formula

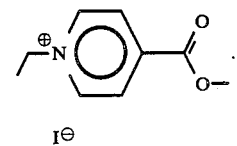

10. The process of claim 9 wherein the determinations are carried out at a constant temperature.

* * * * *